United States Patent
Karp

(10) Patent No.: US 6,697,156 B1
(45) Date of Patent: Feb. 24, 2004

(54) POLARIZED MATERIAL INSPECTION APPARATUS

(76) Inventor: John Karp, 25 Northbrook Dr., Gray, ME (US) 04039

( * ) Notice: Subject to any disclaimer, the term of this patent is extended or adjusted under 35 U.S.C. 154(b) by 0 days.

(21) Appl. No.: 09/543,650

(22) Filed: Apr. 5, 2000

(51) Int. Cl.[7] ................................................. G01J 4/00
(52) U.S. Cl. ....................................................... 356/364
(58) Field of Search .............................. 356/364, 366, 356/367, 369; 250/225

(56) References Cited

U.S. PATENT DOCUMENTS

| | | | | |
|---|---|---|---|---|
| 2,120,365 A | * | 6/1938 | Kriebel ........................... | 88/14 |
| 2,947,212 A | * | 8/1960 | Woods ........................... | 88/14 |
| 3,790,285 A | * | 2/1974 | Swinson ...................... | 356/115 |
| 4,028,728 A | * | 6/1977 | Sharp ........................... | 358/106 |
| 5,053,704 A | * | 10/1991 | Fitzpatrick .................. | 324/235 |
| 5,198,875 A | * | 3/1993 | Bazin et al. ................. | 356/369 |
| 5,442,489 A | * | 8/1995 | Yamamoto et al. .......... | 359/810 |
| 5,532,738 A | * | 7/1996 | Stern ............................ | 348/61 |
| 5,742,392 A | * | 4/1998 | Anderson et al. ........... | 356/364 |
| 5,805,279 A | * | 9/1998 | Palombo et al. ............. | 356/240 |
| 5,815,259 A | * | 9/1998 | Brandon et al. ............ | 356/244 |

* cited by examiner

Primary Examiner—Michael P. Stafira
(74) Attorney, Agent, or Firm—Michael J. Persson; Lawson & Persson P.C.

(57) ABSTRACT

A polarized material inspection device that includes a light source, a first polarizing filter disposed within the optical path of the light source, a frame into which a second polarizing filter is disposed, and a support for positioning the frame such that an object may be viewed through the second polarizing filter. In the preferred embodiment, the first polarizing filter is rotatable through a ninety degree arc such that planes of polarization may be adjusted to be parallel or orthogonal to one another. The preferred embodiment also includes a light illumination assembly having a rotatably mounted linear polarizer at the polarizing output end. This light assembly is attached to a portion of the frame and may be adjusted such that the beam of light is directed to the desired portion of the surface. Within the frame is mounted a fixed linear polarizing filter of sufficient size to allow the entire illuminated surface to be viewed. The frame is mounted to an adjustable support arm that is attached to a tripod or other support to allow the apparatus to be fixed during a given procedure.

20 Claims, 3 Drawing Sheets

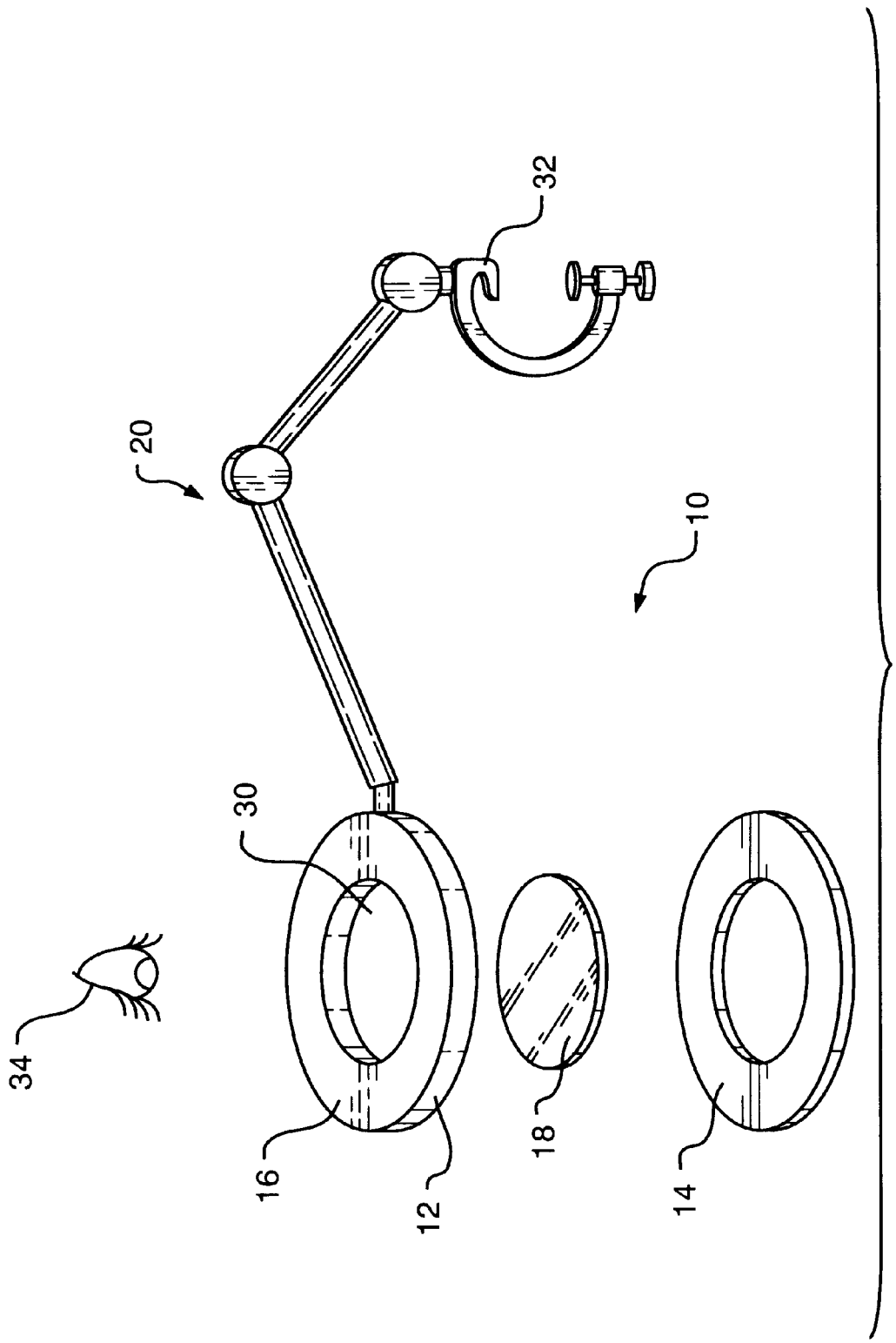

POLARIZED MATERIAL INSPECTION APPARATUS

FIELD OF THE INVENTION

The present invention relates to a device for evaluating the surface and sub-surface properties of a surface and, in particular, to a device for irradiating the surface with adjustable polarized light and viewing the optical reflectance through a polarizing viewer.

BACKGROUND OF THE INVENTION

Light reflected from skin has two components: regular reflectance, or "glare" arising from the surface, and light backscattered from within the tissue. The regular reflectance contains the visual cues related to surface texture, whereas the backscattered component contains the cues related to pigmentation, erythema, infiltrates, vessels and other intracutaneous structures. Unlike the backscattered component, regular reflectance preserves the plane of polarization of polarized incident light. Thus, viewing skin through a linear polarizer, under linearly polarized illumination, separates the two components of tissue reflectance. When the planes of polarization are parallel, images with enhanced surface detail are obtained. When the planes are orthogonal, wrinkles and surface detail disappear, and an enhanced view of vasculature and pigmented lesions is obtained.

The prior art discloses various devices and methods that accomplish surface irradiation and reflection detection. However, none of the prior art devices or methods provide a means or method of illuminating a surface and then view either surface or subsurface reflectance at the discretion of the user. The prior art also requires elaborate and often fixed setups to perform any type of surface analysis. These setups usually require the surface of interest to be moved past a positioned optical array. There is little teaching of portable units that would enable the imaging to be done in remote locations or manipulate the illuminator source with respect to the object being viewed. Finally, most prior art systems are costly and, therefore, are not practical for those with limited resources.

For example, U.S. Pat. No. 2,120,365, issued to Kriebel, discloses the use of polarizing lenses in eyeglasses for orthogonally polarizing light being viewed. The light originates from a source located on the side of an object or material of interest opposite to the viewer, which allows for examining the photo-elastic effects of the light bending around the object.

U.S. Pat. No. 2,947,212 to Woods shows detection of surface conditions of sheet metal by irradiating a surface with polarized light and using a polarizer in the optical path of the detector. This allows for only the viewing the intensity of the polarized light while eliminating all extraneous light rays. Similarly, U.S. Pat. No. 3,904,293 to Gee uses linearly polarized light to irradiate a surface and then detection of the reflected light. Prior to the reflected light being detected, it must first pass through a polarizing beam splitter, which separates the light into its principal polarized (incident) and orthogonally polarized (depolarized) wave components. These two distinct waves are then detected by different detectors, and changes in the surface texture will cause corresponding changes in the detected signal characteristics to be compared.

U.S. Pat. No. 5,053,704, issued to Fitzpatrick, discloses the imaging of a surface to detect cracks, flaws, voids, and the like. To accomplish this detection, a magneto-optical substrate including a conductive sheet is laid over the target material. A current is passed through the conductive sheet to provide a biased magnetic field. Polarized light is then directed through the substrate into the target material and the reflected light is viewed through a separate linear polarizer. The biased magnetic field induces a rotation of the plane of polarization of the incident projected light such that viewing the reflection through a linear polarizer will render flaws visible.

U.S. Pat. No. 5,198,875, issued to Bazin et al., also teaches irradiation of a surface with polarized light. Bazin et al sets up two detectors, one at an angle of reflectance equal to the angle of incident while another detector is located perpendicularly to the surface. The reflected polarized light is passed through polarization separation cubes and eventually four detectors detect the reflected light. These detectors are connected through an electronic processing means, which evaluates the various signals for brightness comparison.

U.S. Pat. No. 5,442,489 to Yamamoto et al relates to a magnifying apparatus. A polarized light irradiates an object and the reflected light is transmitted through a polarizing means and is in turn imaged by an imaging device. This arrangement magnifies and images practical areas of interest.

The article, "Polarized Light Examination and Photography of the Skin" by Rox Anderson, MD, which appeared in the Archives of Dermatology, July 1991, volume 127, pages 1000–1005, describes the above mentioned failings in the art to provide adequate viewing of surface and subsurface epidermis. In response to these failings, the authors of the article developed the polarized material inspection apparatus that is described in U.S. Pat. No. 5,742,392, which is incorporated herein by reference. This apparatus, although providing distinct advantages over prior art systems, has certain attributes that have been seen as drawbacks in some circumstances. First, the use of a head-mounted apparatus, often connected by wires to a power supply, has been found to restrict the movement of physicians utilizing the apparatus. Second, the mounting of a hot lamp in close proximity to the user's head can cause the user to overheat and perspire. Third, head mounting of the unit creates the risk of a user temporarily blinding others within the operating room by inadvertently pointing the light source at the eyes of that person.

Therefore, there is a need for a device for irradiating a surface with polarized light in association with a polarized viewer that provides separation between surface and subsurface reflection, that allows the light source and viewer to be integrally connected, that allows either the surface or subsurface reflectance to be viewed alternatively and at the discretion of the user, that does not restrict the movement of the user or cause the user to perspire, that eliminates the risk of a user temporarily blinding another person by inadvertently pointing the light source at the other person's eyes.

SUMMARY OF THE INVENTION

The present invention is a polarized material inspection device that includes a light source, a first polarizing filter disposed within the optical path of the light source, a frame into which a second polarizing filter is disposed, and a support for positioning the frame such that an object may be viewed through the second polarizing filter. In the preferred embodiment, the first polarizing filter is rotatable through a ninety degree arc such that planes of polarization may be adjusted to be parallel or orthogonal to one another.

However, in other embodiments both filters are rotatable, while in still other embodiments only the second polarizing filter is rotatable.

The preferred embodiment includes a Seymour light illumination assembly having a rotatably mounted linear polarizer at the polarizing output end. This light assembly is attached to a portion of the frame and may be adjusted such that the beam of light is directed to the desired portion of the surface. Within the frame is mounted a fixed linear polarizing filter of sufficient size to allow the entire illuminated surface to be viewed. The frame is mounted to an adjustable support arm that is attached to a tripod or other support to allow the apparatus to be fixed during a given procedure.

In an alternative embodiment of the present invention, a common desktop magnifier is modified to include the above referenced elements. In such an embodiment, the light source is disposed in a ring about the frame, the first polarizing filter is rotatably disposed below the light, and the second polarizing filter is disposed over the magnifying lens. In these embodiments, it is preferred that the second polarizing filter be a flexible sheet of polarizing film that is fixed to the lens.

It is an aspect of the invention to provide a device for irradiating a surface with polarized light in association with a polarized viewer that provides separation between surface and subsurface reflection.

It is another aspect of the invention to provide a device for irradiating a surface in which the light source and viewer may be integrally connected.

It is another aspect of the invention to provide a device for irradiating a surface that allows either the surface or subsurface reflectance to be viewed alternatively and at the discretion of the user.

It is another aspect of the invention to provide a device for irradiating a surface that does not restrict the movement of the user.

It is another aspect of the invention to provide a device for irradiating a surface that does not cause the user to perspire.

It is another aspect of the invention to provide a device for irradiating a surface that eliminates the risk of a user temporarily blinding another person by inadvertently pointing the light source at the other person's eyes.

These aspects of the invention are not meant to be exclusive and other features, aspects, and advantages of the present invention will be readily apparent to those of ordinary skill in the art when read in conjunction with the following description, appended claims and accompanying drawings.

BRIEF DESCRIPTION OF THE DRAWINGS

FIG. 3 is an isometric view of an alternative embodiment of the device of the present invention.

DETAILED DESCRIPTION OF THE INVENTION

Figure 1:
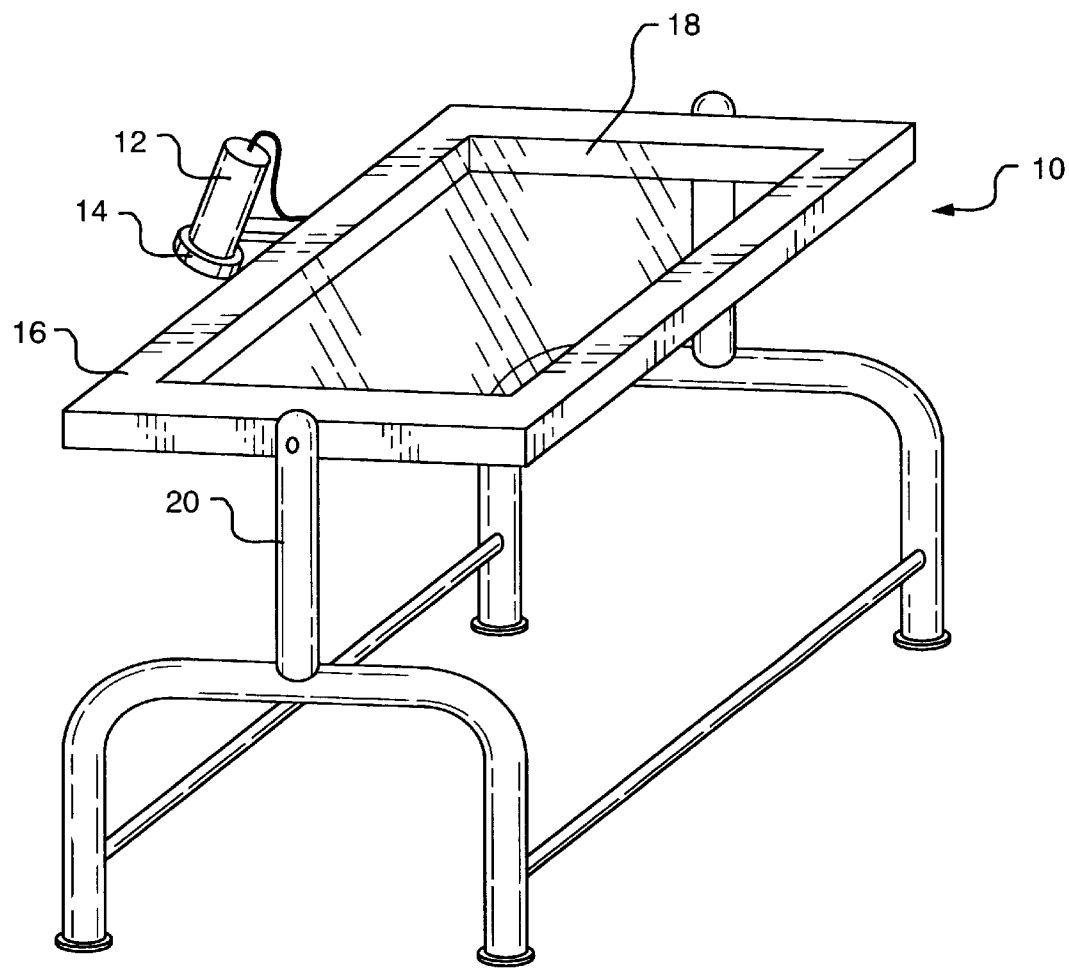
FIG. 1 is an isometric view of the basic embodiment of the device of the present invention.

Referring first to FIG. 1, an isometric view of the basic embodiment of the device 10 is shown. The basic embodiment includes a light source 12, a first polarizing filter 14 disposed within the optical path of the light source, a frame 16 into which a second polarizing filter 18 is disposed, and a support 20 for positioning the frame 16 such that an object (not shown) may be viewed through the second polarizing filter 18. The first polarizing filter 14 and second polarizing filter 18 each have a plane of polarization, and the first polarizing filter 14 and/or the second polarizing filter 18 are rotatable through a ninety degree arc, such that the planes of polarization may be adjusted to be parallel or orthogonal to one another.

As shown in FIG. 1, it is preferred that the light source 12 be attached to the frame 16 and positioned such that the light from the light source 12 is reflected back through the second polarizing filter 18. In this embodiment, the first polarizing filter 14 is mounted directly to the light source 12 and is rotatable through a ninety-degree arc. However, it is understood that other embodiments may include a first polarizing filter 14 mounted separately from the light source 12. FIG. 1 also shows the support 20 being a table to which the frame 16 is rotatably mounted. It is noted, however, that this support 20 may be varied in other embodiments to provide proper positioning for different objects to be viewed.

In operation, the device 10 will be positioned relative to an object to be viewed, the light source 12 will be energized and the light will be polarized by the first polarizing filter 14 and will pass on to illuminate the object. The light will then be reflected off of the object and will pass through the second polarizing filter 18 for viewing by the user. Depending upon the details to be viewed, the first polarizing filter 14 may be rotated into a parallel relationship to the second polarizing filter 18, or may be rotated into an orthogonal relationship to the second polarizing filter 18.

Figure 2:
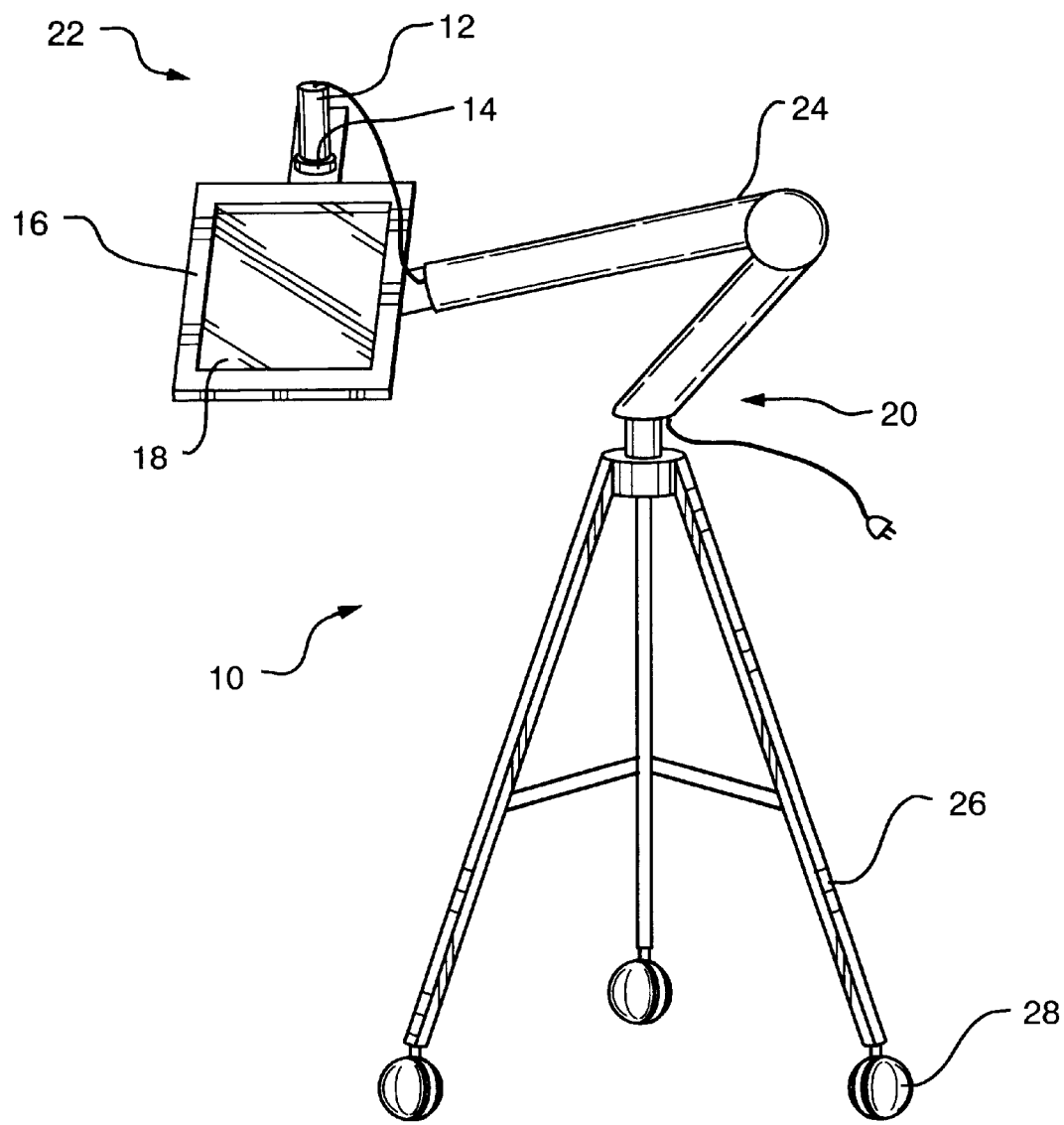
FIG. 2 is an isometric view of the preferred embodiment of the device of the present invention.

Referring now to FIG. 2, the preferred embodiment of the device 10 of the present invention is shown. In this embodiment, the light source 12 and first polarizing filter 14 are included in a single Seymour light illumination assembly 22. The preferred frame 16 is mounted to a support 20 that includes an adjustable arm 24 and a tripod 26 to which the adjustable arm 24 is attached. The adjustable arm 24 and tripod 26 of the preferred support 20 allow the user to manipulate the frame 16 to a wide range of positions in order to illuminate the desired surface and to allow the user to view the surface through the second polarizing filter 18. As also shown in FIG. 2, the support 20 may include a plurality of casters 28, or other movement aids such as wheels, glides, or the like, to allow the device 10 to be easily moved and positioned relative to the surface to be viewed.

Referring now to FIG. 3, an exploded isometric view of an alternative embodiment of the device 10 is shown. In this embodiment, a common desktop magnifier may be modified to produce a device 10 in accordance with the present invention.

As shown in FIG. 3, an adjustable arm 24 is provided with an attachment for attaching the device 10 to a desk or other surface. The adjustable arm 24 is rotatably attached to the frame 16, allowing the device to be manipulated to a wide range of positions. The frame 16 is a preferably of substantially cylindrical and includes a central opening into which a magnifying lens 30 is mounted. A light source 12 is attached between the underside of the frame 16 between and a first polarizing filter 14. The first polarizing filter 14 is dimensioned to mate with, and rotatably attached to the underside of the frame 16. The second polarizing filter 18 is dimensioned to mate with the magnifying lens 30 and is secured in a mating relationship with the lens 30. In the embodiment of FIG. 3, the second polarizing filter 18 is preferably a flexible polarizing film that is adhered directly to the undersurface of the lens 30. In other embodiments, however, the second polarizing filter 18 may be a glass filter secured to the underside of the frame 16 via mechanical means.

In operation, a user will position the device 10 in the desired position relative to the surface to be viewed and position their eye 34 above the magnifying lens 30 to view the surface. The first polarizing filter 14 may then be rotated such that the planes of polarization of the first polarizing filter 14 and the second polarizing filter 18 are in parallel relation to one another and to be rotated again such that the planes of polarization are in orthogonal relation.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. A polarized material inspection apparatus for viewing a material with a polarized light, said apparatus comprising:
    a light source having an optical path,
    a first polarizing filter disposed within the optical path of said light source,
    a frame,
    a second polarizing filter and a magnifying lens disposed within said frame, and
    a support attached to said frame for positioning said frame.

2. The polarized material inspection apparatus of claim 1 wherein said support comprises a table.

3. The polarized material inspection apparatus of claim 2 wherein said frame is rotatably attached to said table.

4. The polarized material inspection apparatus of claim 1 wherein said support comprises a tripod.

5. The polarized material inspection apparatus of claim 4 further comprising an arm mounted to said tripod, wherein said frame is mounted to said arm.

6. The polarized material inspection apparatus of claim 5 wherein said arm is an adjustable arm.

7. The polarized material inspection apparatus of claim 6 wherein said tripod comprises a plurality of casters.

8. The polarized material inspection apparatus of claim 1 wherein said support comprises an adjustable arm.

9. The polarized material inspection apparatus of claim 1 wherein said frame comprises and underside, and wherein said light source is mounted to said underside of said frame.

10. The polarized material inspection apparatus of claim 9 wherein said first polarizing filter is attached to underside of said frame, and wherein said light source is disposed between said underside of said frame and said first polarizing filter.

11. The polarized material inspection apparatus of claim 10 wherein said first polarizing filter is rotatably attached to said underside of said frame.

12. The polarized material inspection apparatus of claim 1 wherein said second polarizing filter is attached to said magnifying lens.

13. The polarized material inspection apparatus of claim 12 wherein said second polarizing filter is a flexible polarizing film that is adhered directly to said magnifying lens.

14. The polarized material inspection apparatus of claim 1 wherein said support comprises a tripod.

15. The polarized material inspection apparatus of claim 4 further comprising an arm mounted to said tripod, and wherein said frame is mounted to said arm.

16. The polarized material inspection apparatus of claim 1 wherein said frame comprises and underside, and wherein said light source is mounted to said underside of said frame.

17. The polarized material inspection apparatus of claim 16 wherein said first polarizing filter is rotatably attached to said underside of said frame.

18. A polarized material inspection apparatus for allowing a user to view a material with a polarized light, said apparatus comprising:
    a light source having an optical path,
    a first polarizing filter disposed within the optical path of said light source,
    a frame,
    a second polarizing filter disposed within said frame, and
    a support attached to said frame for positioning said frame, wherein said support is independent of said user and is dimensioned to be fixed in a position allowing said user to view said material through said frame.

19. The polarized material inspection apparatus of claim 18 wherein said support comprises a table.

20. The polarized material inspection apparatus of claim 19 wherein said frame is rotatably attached to said table.

\* \* \* \* \*